United States Patent
Gu et al.

(10) Patent No.: US 8,810,550 B2
(45) Date of Patent: Aug. 19, 2014

(54) OPTICAL TOUCH DEVICE AND PORTABLE ELECTRONIC DEVICE WITH HEART RATE MEASURING FUNCTION AND METHOD FOR INCREASING ACCURACY OF HEART RATE MEASUREMENT

(75) Inventors: Ren-Hau Gu, Hsin-Chu (TW); Yu-Hao Huang, Hsin-Chu (TW); Hsin-Chia Chen, Hsin-Chu (TW); Ming-Tsan Kao, Hsin-Chu (TW); Sen-Huang Huang, Hsin-Chu (TW)

(73) Assignee: PixArt Imaging Inc., Science-Based Industrial Park, Hsin-Chu (TW)

( * ) Notice: Subject to any disclaimer, the term of this patent is extended or adjusted under 35 U.S.C. 154(b) by 95 days.

(21) Appl. No.: 13/561,088

(22) Filed: Jul. 30, 2012

(65) Prior Publication Data
US 2013/0100081 A1    Apr. 25, 2013

(30) Foreign Application Priority Data
Oct. 19, 2011   (TW) .............................. 100137850 A

(51) Int. Cl.
*G06F 3/042*       (2006.01)
*A61B 5/024*       (2006.01)
*A61B 5/00*        (2006.01)

(52) U.S. Cl.
CPC .......... *A61B 5/02416* (2013.01); *A61B 5/6897* (2013.01)
USPC .......................................... 345/175

(58) Field of Classification Search
USPC .......................................... 345/175
See application file for complete search history.

(56) References Cited

U.S. PATENT DOCUMENTS

2010/0198073 A1*  8/2010 Nishihara et al. ............. 600/443
2013/0179911 A1*  7/2013 Dang et al. ...................... 725/12

* cited by examiner

*Primary Examiner* — Fred Tzeng
(74) *Attorney, Agent, or Firm* — Winston Hsu; Scott Margo

(57) ABSTRACT

Method for increasing accuracy of heart rate measuring includes sensing a finger of a user for generating sensed images of the finger, obtaining displacement information of the finger according to the sensed images, then using the motion information to compensate the sensed images of the finger, and finally using brightness variation of the compensated sensed images of the finger to measure heart rate of the user.

18 Claims, 2 Drawing Sheets

OPTICAL TOUCH DEVICE AND PORTABLE ELECTRONIC DEVICE WITH HEART RATE MEASURING FUNCTION AND METHOD FOR INCREASING ACCURACY OF HEART RATE MEASUREMENT

BACKGROUND OF THE INVENTION

1. Field of the Invention

The present invention relates to an optical touch device, and particularly relates to an optical touch device with heart rate measuring function, a portable electronic device with the optical touch device and related methods.

2. Description of the Prior Art

A portable electronic device such as a mobile phone is popularly used now. Under keen competition, each manufacturer does their best to add new functions to the portable electronic device. Most modern mobile phones have touch sensing function, such that the user can directly perform some operation on the screen such as dialing number. Various kinds of application software are developed corresponding to the touch sensing function. One of them can be utilized to measure the heart rate and pulses of the user. The accuracy for measuring heart rate is limited due to the limitation of mobile phone hardware, however. If higher accuracy is desired, a professional device such as a pulse oximeter is needed. Such device is expensive and not easy to carry about like a mobile phone. Thus there is no better solution for the user now.

SUMMARY OF THE INVENTION

One embodiment of the present invention provides an optical touch device with heart rate measuring function. The optical touch device comprises: an image sensor, for reflecting reflected light of specific light while sensing an pointer touching the optical touch device, to generate an image signal related with the pointer; and a specific frequency extractor, for acquiring a frequency signal and a displacement signal according to a plurality of the image signals related with the pointer, to generate heart rate information; wherein the specific frequency extractor simultaneously separates displacement variation part indicated by the image signals according to brightness variation part indicated by the image signals to acquire the frequency signal; wherein the frequency signal indicates frequency in a specific frequency region, where the displacement signal indicates displacement information generated when the pointer touches the optical touch device.

Another embodiment of the present invention provides a portable electronic device with heart rate measuring function. The portable electronic device comprises: an optical touch device comprising: an image sensor, for reflecting reflected light of specific light while sensing an pointer touching the optical touch device, to generate an image signal related with the pointer; and a specific frequency extractor, for acquiring a frequency signal and a displacement signal according to a plurality of the image signals related with the pointer, to generate heart rate information; wherein the specific frequency extractor simultaneously separates displacement variation part indicated by the image signals according to brightness variation part indicated by the image signals to acquire the frequency signal. The frequency signal indicates frequency in a specific frequency region, and the displacement signal indicates displacement information generated when the pointer touches the optical touch device. The portable electronic device further comprise a display panel and a processor. The display panel displays a target objective. The processor controls a location for the target objective in the display panel, according to the displacement signal indicating the displacement variation part of the pointer.

Another embodiment of the present invention provides a method for increasing heart rate measuring accuracy. The method comprises: reflecting reflected light of specific light while sensing an pointer touching a optical touch device, to generate an image signal related with the pointer; and acquiring a frequency signal and a displacement signal according to a plurality of the image signals related with the pointer, to generate heart rate information; wherein the step of acquiring the frequency signal simultaneously separates displacement variation part indicated by the image signals according to brightness variation part indicated by the image signals to acquire the frequency signal. The frequency signal indicates frequency in a specific frequency region, and the displacement signal indicates displacement information generated when the pointer touches the optical touch device.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
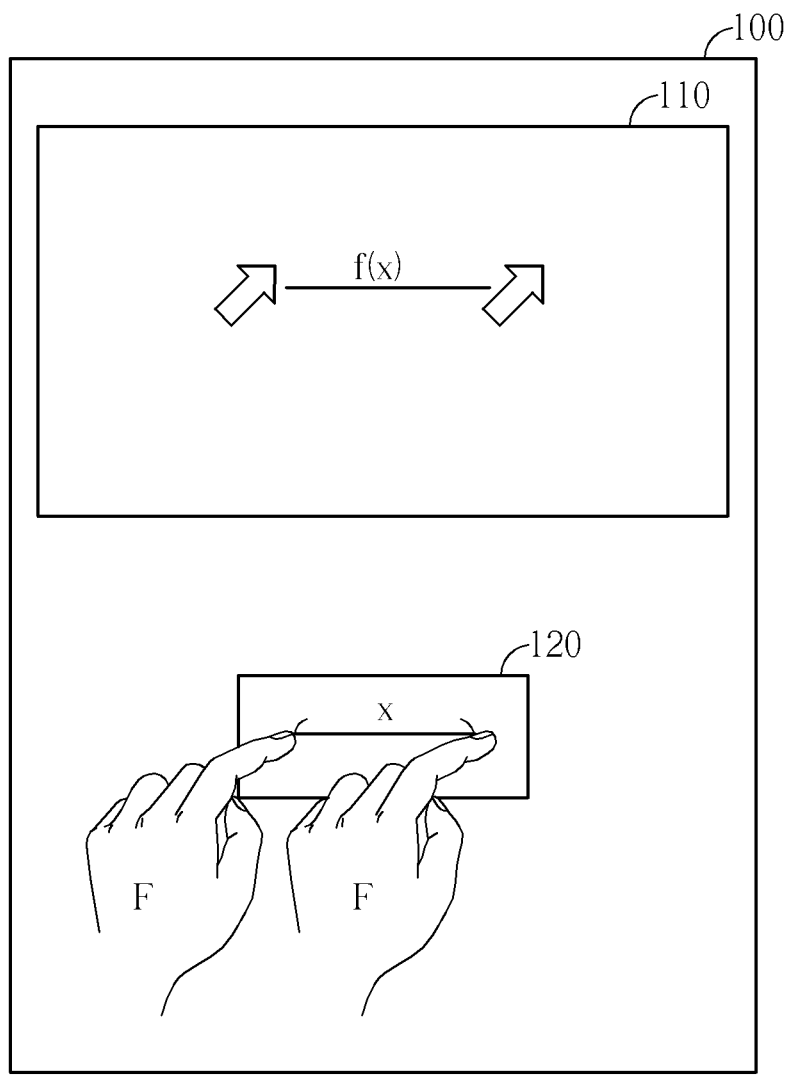
FIG. 1 is a schematic diagram illustrating a portable electronic device with heart rate measuring function according to the present invention.

FIG. 1 is a schematic diagram illustrating a portable electronic device with heart rate measuring function according to the present invention. Please note some devices that are not key components for the present invention such as a keypad or an amplifier are omitted for brevity, since the main purpose of FIG. 1 is to depict how the portable electronic device 100 is utilized by a user. The portable electronic device 100 includes a display panel 110 and an optical touch device 120. The display panel 110 displays a target objective C such as a cursor. If a user wants to move the cursor C, he/she can put the finger F (pointer) on the optical touch device 120 and moves it. The cursor C moves when the optical touch device 120 senses the motion of the user finger F. Additionally, the portable electronic device 100 can utilize indirect touch. That is, the cursor C moves for f(X) when the finger F moves for X on the optical touch device 120. f(X) is a function of X, and the value thereof is substantially larger than X. By this way, the area of the optical touch device 120 can be less than which of the display panel 110 to save cost.

Figure 2:
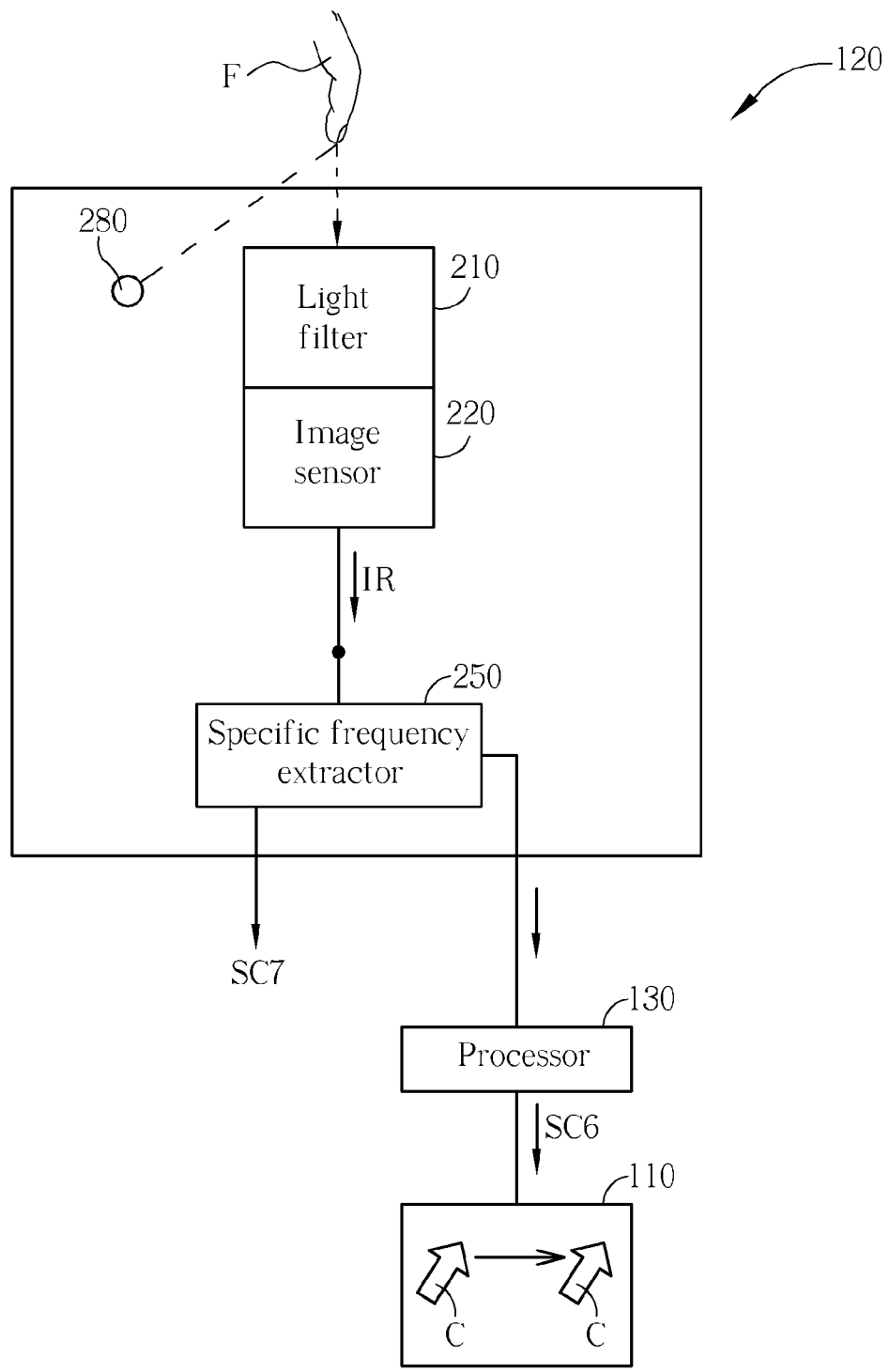
FIG. 2 is schematic diagram illustrating an optical touch device with heart rate measuring function according to the present invention.

FIG. 2 is schematic diagram illustrating an optical touch device 120 with heart rate measuring function according to the present invention. The optical touch device 120 includes a light filter 210, an image sensor 220, a specific frequency extractor 250 and a light source 280. The light filter 210 filters light with specific light band, such as the light band for visible light. Therefore, the light band of the light sensed by the image sensor 220 is almost unfiltered light band such as the light band for invisible light (infrared light). By this way, the light source 280 emits invisible light, which is reflected by the finger F, through the light filter 210, to reach the image sensor 220. That is, the light filter 210 only allows specific light to be sensed by the image sensor 220.

The specific frequency extractor 250 simultaneously separates displacement variation part indicated by the image signals according to brightness variation part indicated by the image signals to acquire the frequency signal. The frequency signal indicates frequency in a specific frequency region. The displacement signal indicates displacement information generated when the pointer touches the optical touch device. Specifically, the specific frequency extractor 250 receives the sensed image IR generated by the image sensor 220, and determines the motion track (i.e. the movement direction and distance) according to continuous sensed image IR variation, to thereby generate/acquire a displacement signal (the displacement information generated when the pointer touches the optical touch device 120). For example, the finger F will be sensed by the image sensor 220 to generate a specific pattern such as finger print. At the timing of T1, the location for the specific pattern in the sensed image IR is (X1, Y1); at the timing of T2, the location for the specific pattern in the sensed image IR is (X2, Y2). Thereby the specific frequency extractor 250 can compare these two sensed images to acquire the displacement information (X1-X2,Y1-Y2).

After that, the specific frequency extractor 250 simultaneously separates displacement variation part indicated by sensed images IR according to brightness variation part indicated by continuous sensed images IR, according to the sensed images IR generated by the image sensor 220. The frequency signal indicates frequency in a specific frequency region corresponding to heart rate. Preferably, the specific frequency region can be smaller than 250 Hz. Alternatively, the specific frequency extractor 250 can be regarded a device utilizing a motion vector (i.e. the displacement information) generated by a plurality of sensed images IR to compensate a signal for the image sensed by specific light, to generate the frequency signal and to generate heart rate information SC7. Practically, the specific frequency extractor 250 separates displacement variation part according to ICA (independent component analysis) or BSS (blind source separation) while separating displacement variation part.

The operation of heart rate measuring is based on blood at the fingertip. The amount of blood, which is varied corresponding to the speed that blood flows in/out the blood vessel due to the pulse generated by heartbeat, affects light absorbing rate. For example, oxygen amount contained in blood, oxygen capacity and blood capacity all vary corresponding to heartbeats. Accordingly, different brightness is sensed by the images sensor 220 when the finger F is in the sensed region of the images sensor 220, since the blood amount of finger F is different. By this way, the specific frequency extractor 250 can compute heart rate to acquire heart rate information SC7 according to the brightness number in the sampling period.

Additionally, it should be noted that the specific frequency extractor 250 also computes heart rate based on the displacement information. The image sensor 220 senses brightness variation of the sensed image IR if the finger F moves. Accordingly, the computing of the heart rate may have error due to the finger F movement, if only the brightness variation of the sensed image IR is utilized to compute heart rate. Therefore, the present invention further considers the effect caused by the finger F movement besides the brightness variation of sensed images IR while computing heart rate. For this reason, the specific frequency extractor 250 utilizes the motion vector indicated by displacement information (i.e. displacement variation part) to compensate difference of the sensed image IR caused by the finger F movement, to thereby acquire more accurate heart rate information SC7.

However, an un-countable state for heart rate may exist if the movement level for the finger F is too high (i.e. the motion vector is too high). For example, the finger F has left the range that the image sensor can sense, thus a threshold value can be set in the present invention. The sensed heart rate information can be regarded as useless or the computing thereof must be stopped if the motion vector (the displacement variation part) is over the threshold value. Or, the user will be informed to move their finger to a suitable location such that the specific frequency extractor 250 can restart the heart rate measuring.

Moreover, the portable electronic device 100 further includes a processor 130. The processor 130 receives above-mentioned motion vector and fits it to a predetermined algorithm to generate a control signal SC6, to thereby move the cursor C on the display panel 110. For example, if the finger F moves X for left on the touch device 120, the processor 130 can control the cursor C to move X or 2X for left, depending on the design of algorithm.

In view of above-mentioned description, the present invention can be classified into two operation modes: normal mode and heart rate detecting mode. In the normal mode, the specific frequency extractor 250 can stop operating, and the user can randomly move their finger to move the cursor on the display panel 110. In the heart rate detecting mode, the specific frequency extractor 250 starts operating and the user can not randomly move their finger in this mode, since the controller 130 will control the display panel to show detecting fail or need to be redetected if the movement level of the finger F is too high. Via this control mechanism, the measured heart rate information can have higher accuracy.

Moreover, for practical implement, a lens and a aperture can be provided at the front end of the image sensor. The detail description therefore is omitted since such devices are not key components of the present invention and are well known by persons skilled in the art. If better sensing quality is desired, light source intensity can be increased or the aperture can be enlarged to reach such requirement.

In view of above-mentioned embodiment, the optical touch device of the present invention can further provide heart rate measuring function besides touch control function. Besides, high accurate heat rate measuring can be acquired via detecting displacement variation part (the motion vector) to compensate the sensed image sensed while detecting heart rate. Additionally, the user can measure heart rate at any time and have great convenience, since the above-mentioned embodiments can be applied to a portable mobile phone.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An optical touch device with heart rate measuring function, comprising:
   an image sensor, for reflecting reflected light of specific light while sensing an pointer touching the optical touch device, to generate a plurality of image signals related with the pointer; and
   a specific frequency extractor, for acquiring a frequency signal and a displacement signal according to the image signals related with the pointer, to generate heart rate information;
   wherein the specific frequency extractor simultaneously separates displacement variation part indicated by the image signals according to brightness variation part indicated by the image signals to acquire the frequency signal;
   wherein the frequency signal indicates frequency in a specific frequency region, where the displacement signal indicates displacement information generated when the pointer touches the optical touch device.

2. The optical touch device of claim 1, wherein the specific frequency extractor stops computing the frequency signal when the displacement variation part is larger than a predetermined value.

3. The optical touch device of claim 1, wherein the specific frequency region corresponds to heart rate frequency, preferably the specific frequency region is smaller than 250 Hz.

4. The optical touch device of claim 1, wherein the specific frequency extractor utilizes a motion vector formed by the image signals to compensate a signal of an image sensed by the specific light to accordingly generate the frequency signal.

5. The optical touch device of claim 1, further comprising a light filter to limit that only the specific light can be sensed by the image sensor.

6. The optical touch device of claim 1, wherein the specific frequency extractor separates the displacement variation part according to an ICA function.

7. The optical touch device of claim 1, wherein the specific light is invisible light.

8. A portable electronic device with heart rate measuring function, comprising:
   an optical touch device, comprising:
      an image sensor, for reflecting reflected light of specific light while sensing an pointer touching the optical touch device, to generate a plurality of image signals related with the pointer; and
      a specific frequency extractor, for acquiring a frequency signal and a displacement signal according to the image signals related with the pointer, to generate heart rate information;
      wherein the specific frequency extractor simultaneously separates displacement variation part indicated by the image signals according to brightness variation part indicated by the image signals to acquire the frequency signal;
      wherein the frequency signal indicates frequency in a specific frequency region, where the displacement signal indicates displacement information generated when the pointer touches the optical touch device;
   a display panel, for displaying a target objective; and
   a processor, for controlling a location for the target objective in the display panel, according to the displacement signal indicating the displacement variation part of the pointer.

9. The portable electronic device of claim 8, wherein the specific frequency extractor stops computing the frequency signal when the displacement variation part is larger than a predetermined value.

10. The portable electronic device of claim 8, wherein the specific frequency region corresponds to heart rate frequency, preferably the specific frequency region is smaller than 250 Hz.

11. The portable electronic device of claim 8, wherein the specific frequency extractor utilizes a motion vector formed by the image signals to compensate a signal of an image sensed by the specific light to accordingly generate the frequency signal.

12. The portable electronic device of claim 8, further comprising a light filter to limit that only the specific light can be sensed by the image sensor.

13. The portable electronic device of claim 8, wherein the specific frequency extractor separates the displacement variation part according to an ICA function.

14. The portable electronic device of claim 8, wherein the specific light is invisible light.

15. A method for increasing heart rate measuring accuracy, comprising:
   reflecting reflected light of specific light while sensing an pointer touching an optical touch device, to generate a plurality of image signals related with the pointer; and
   acquiring a frequency signal and a displacement signal according to the image signals related with the pointer, to generate heart rate information;
   wherein the step of acquiring the frequency signal simultaneously separates displacement variation part indicated by the image signals according to brightness variation part indicated by the image signals to acquire the frequency signal;
   wherein the frequency signal indicates frequency in a specific frequency region, where the displacement signal indicates displacement information generated when the pointer touches the optical touch device.

16. The method of claim 15, further comprising:
   stopping computing the frequency signal when the displacement variation part is larger than a predetermined value.

17. The method of claim 15, wherein the specific frequency region corresponds to heart rate frequency, preferably the specific frequency region is smaller than 250 Hz.

18. The method of claim 15, wherein the step of acquiring the frequency signal further comprises:
   utilizing a motion vector formed by the image signals to compensate a signal of an image sensed by the specific light to accordingly generate the frequency signal.

* * * * *